United States Patent
Chien et al.

(10) Patent No.: US 6,261,764 B1
(45) Date of Patent: Jul. 17, 2001

(54) BUFFERS FOR STABILIZING ANTIGENS

(75) Inventors: David Y. Chien, Alamo; Phillip Arcangel, Berkeley, both of CA (US); Stephen Tirell, Franklin; Wanda Zeigler, Medway, both of MA (US)

(73) Assignee: Chiron Corporation, Emeryville, CA (US)

( * ) Notice: Subject to any disclaimer, the term of this patent is extended or adjusted under 35 U.S.C. 154(b) by 0 days.

(21) Appl. No.: 09/158,815

(22) Filed: Sep. 22, 1998

Related U.S. Application Data

(60) Provisional application No. 60/059,703, filed on Sep. 22, 1997.

(51) Int. Cl.$^7$ .............................. C12Q 1/70; G01N 33/53
(52) U.S. Cl. .................. 435/5; 436/18; 436/176
(58) Field of Search ................. 435/5; 436/518, 436/820, 18, 176

(56) References Cited

U.S. PATENT DOCUMENTS

| | | | |
|---|---|---|---|
| 4,511,502 | * | 4/1985 | Builder et al. . |
| 4,658,022 | * | 4/1987 | Knowles ............................ 530/402 |
| 4,678,553 | * | 7/1987 | Mandle et al. . |
| 4,737,453 | | 4/1988 | Primus ................................... 435/5 |
| 4,847,081 | * | 7/1989 | Rice ...................................... 424/89 |
| 5,616,460 | | 4/1997 | Figard ................................... 435/5 |
| 5,681,695 | | 10/1997 | Decker et al. ......................... 435/5 |
| 5,705,330 | | 1/1998 | Shah et al. ........................... 435/5 |
| 5,773,212 | | 6/1998 | Figard ................................... 435/5 |

FOREIGN PATENT DOCUMENTS

| | | |
|---|---|---|
| 195 02 386 A1 | 8/1996 | (DE) . |
| 0 341 439 | 11/1989 | (EP) . |
| 2 556 840 | 6/1985 | (FR) . |
| WO 92/08979 | 5/1992 | (WO) . |
| WO 93/00365 | 1/1993 | (WO) . |
| WO 93/14403 | 7/1993 | (WO) . |
| WO 94/24560 | 10/1994 | (WO) . |
| WO 94/25874 | 11/1994 | (WO) . |
| WO 94/26932 | 11/1994 | (WO) . |
| WO 95/27702 | 10/1995 | (WO) . |
| WO 97/44469 | 11/1997 | (WO) . |

OTHER PUBLICATIONS

Chien et al., "Diagnosis of hepatitis C virus (HCV) infection using an immunodominant chimeric polyprotein to capture circulating antibodies: Reevaluation of the role of HCV in liver disease," *Proc. Natl. Acad. Sci. USA*, 1992, 89, 10011–10015.

Choo et al., "Isolation of a cDNA Clone Derived from a Blood–Borne Non–A, Non–B Viral Hepatistis Genome, "*Science*, 244, 359–362.

Cousens et al., "High level expression of proinsulin in the yeast, *Saccharomyces cerevisiae*," *Gene*, 1987, 61, 265–275.

Ebeling et al., "Second–generation RIB A to confirm diagnosis of HCV infection," *Lancet*, 1991, 337, 912–913.

Kotwal et al., "Detection of acute hepatitis C virus infection by ELISA using a synthetic peptide comprising a structural epitope," *Proc. Natl. Acad. Sci. USA*, 1992, 89, 4486–4489.

Kuo et al., "An Assay for Circulating Antibodies to a Major Etiologic Virus of Human Non–A, Non–B Hepatitis,"*Science*, 1989, 244, 362–364.

Sallberg et al., "Immunodominant Regions within the Hepatitis C Virus Core and Putative Matrix Proteins,"*J. Clin. Microbiol.*, 1992, 30(8), 1989–1994.

Cohard, M. et al., "Hepatitis C virus–specific CTL respones in PBMC from chimpanzees with chronic hepatitis C: determination of CTL and CTL precursor frequencies using a recombinant canarypox virus (ALVAC)", *J. Immunol. Methods*, 1998, 214(1–2), 121–129.

Ide, Y. et al., "Hepatitis C virus NS5A protein is phosphorylated in vitro by a stabley bound protein kinase from HeLa cells and by cAMP–dependent protein kinase A–alpha catalytis subunit", *Gene*, 1997, 201(1–2), 151–158.

Patent Abstracts of Japan, JP 06–074956 A, published Mar. 18, 1994, 1 page.

* cited by examiner

*Primary Examiner*—Donna C. Wortman
(74) *Attorney, Agent, or Firm*—Paul K. Legaard; Alisa A. Harbin; Robert P. Blackburn

(57) ABSTRACT

The present invention is directed to an antigen diluent or buffer for antigens, in particular HCV recombinant antigens, comprising a reducing agent. The antigen diluent or buffer serves as a stabilizing buffer for the antigens. The present invention is also directed to antigen diluents or buffers for use in an automated immunoassay.

29 Claims, No Drawings

BUFFERS FOR STABILIZING ANTIGENS

This application claims priority benefit under 35 U.S.C. §119 to application Ser. No. 60/059,703, filed Sep. 22, 1997, hereby incorporated by reference in its entirety.

FIELD OF THE INVENTION

The present invention is related generally to the field of immunoassays and specifically to buffers for stabilizing antigens, in particular hepatitis C virus (HCV) antigens, for use in anti-HCV immunoassays.

BACKGROUND OF THE INVENTION

In general, immunoassays are produced by first determining epitopes that are specifically associated with a virus and then determining which of the epitopes is preferred for the assay being developed. When the particular epitopes are isolated, their sequences are determined, and genetic material for producing the epitopes is produced. Methods of producing proteins by either chemical or biological means are known, as are assays used to detect the presence of antibodies to particular epitopes. Highly selective and sensitive immunoassays generally contain major immunodominant epitopes of the pathogen suspected of infecting a patient.

For the virus HCV, major immunodominant linear epitopes have been identified from the core, NS3 (conatructural), NS4 and NS5 regions of the virus polyprotein. HCV core protein and putative matrix proteins have been assayed against human serum samples containing antibodies to HCV and several immunodominant regions within the HCV proteins have been defined. Sallberg, et al., *J. Clin. Microbiol.*, 1992, 30, 1989–1994, incorporated by reference herein in its entirety. Protein domains of HCV-1 polyproteins including domains C, E1, E2/NS1, NS2, NS3, NS4, and NS5 have been identified and their approximate boundaries have been provided in WO 93/00365, incorporated by reference herein in its entirety. In addition, individual polypeptides having sequences derived from the structural region of HCV have been designed in order to obtain an immunodominant epitope useful in testing sera of HCV patients. Kotwal, et al., *Proc. Natl. Acad. Sci. USA*, 1992, 89, 4486–4489, incorporated by reference herein in its entirety.

The current assay of choice for HCV antibody detection is the Ortho 3.0 ELISA, a manual assay. Chiron-produced recombinant HCV antigens for use in the ELISA are c200 (ns-3, c100), c22 and NS-5. The c33c and c22 antigens are very immunogenic. Antibodies to c33c and c22 are also found in early seroconversion panels. The prevalence of HCV antibodies varies from 58% to 95% with the highest detection rate obtained for the c33c polypeptide followed by the c22 polypeptide. Chien. et al., *Proc. Natl. Acad. Sci. USA*, 1992, 89, 10011–10015, incorporated by reference herein in its entirety. However, problems of stabilizing HCV antigens in the liquid phase have been encountered. The lack of stability of HCV antigens in the liquid phase is a major disadvantage of the current HCV antibody detection assay. Therefore, developing an antigen buffer for the anti-HCV immunoassay has been attempted utilizing the same antigens as the Ortho 3.0 ELISA wherein the buffer stabilizes the HCV antigens. In addition, adapting the reagents, buffer and protocols to already existing automated machines, such as the ACS:Centaur has been attempted. Accordingly, there is currently a need to improve the stability of HCV antigens in the liquid phase for use in anti-HCV immunoassays. Such improved assay reagents and methods provide for better detection of HCV antibodies in screening of blood supplies and other biological fluids. It is contemplated that the buffers be can used for other antigens which may be unstable in the liquid phase, e.g. human immunodeficiency virus (HIV) antigens

SUMMARY OF THE INVENTION

In one aspect, the present invention is directed to an antigen diluent or buffer capable of stabilizing antigens in the liquid phase, in particular HCV recombinant antigens, comprising a reducing agent.

In another aspect, the present invention is directed to immunoassays using an antigen diluent or buffer containing a reducing agent.

In another aspect, an improved immunoassay kit is provided, the improvement comprising using an antigen diluent or buffer for HCV antigens containing a reducing agent.

DETAILED DESCRIPTON OF THE INVENTION

The practice of the present invention will employ, unless otherwise indicated, conventional methods of virology, immunology, microbiology, molecular biology and recombinant DNA techniques within the skill of the art. Such techniques are explained fully in the literature. See, e.g., Sambrook, et al., *Molecular Cloning: A Laboratory Manual* (2nd Edition, 1989); *DNA Cloning: A Practical Approach*, Vols. I & II (D. Glover, ed.); *Methods In Enzymology* (S. Colowick and N. Kaplan eds., Academic Press, Inc.); *Handbook of Experimental Immunology*, Vols. I–IV (D. M. Weir and C. C. Blackwell eds., Blackwell Scientific Publications); and *Fundamental Virology*, 2nd Edition, Vols. I & II (B. N. Fields and D. M. Knipe, eds.).

Reagent stability over time is a critical issue. The c33c antigen diluted in buffer and tested the same day was functional using Magic Lite Assay protocols described below. However the reagent, when stressed at 37° C., lost more than 50% immunoreactivity to early seroconversion panels. The c33c in the liquid phase may slowly "aggregate" or become insoluble. Known components were tried in order to stabilize c33c immunoreactivity such as sugars, gelatin, glycerol, cross-linking reagents and anti-oxidants. It was discovered that keeping the c33c antigen in the reduced form can maintain immunoreactivity for periods over 24 hours, even up to at least 7 days, at 37° C. on early c33c seroconversion panels (matching Ortho 3.0 ELISA performance). The reducing agent reduces the disulfide bonds among cysteine groups within the c33c molecule, perhaps improving c33c immunoreativity and solubility. There was no indication of antigen stability at 37° C. for such lengths of time of conventional lite reagents in the liquid phase prior to the advent of the antigen diluent for c33c. Similar experiments were performed for c200 and a multiple epitope fusion antigen (MEFA-6) as shown below. Thus, the present invention provides antigen diluents or buffers for stabilizing HCV antigens for use in anti-HCV immunoassays. The antigen diluents or buffers of the present invention can be used in immunoassays such as, for example, ELISA and CLIA.

The present invention is directed to antigen diluents or buffers providing for improved stability of HCV antigens in the liquid phase. As used herein, "antigen diluents or buffers" refers to the solution in which the antigen is contained; it may or may not possess buffering capacity. In particular, the invention is directed to antigen diluents or buffers for improved stability for the recombinant HCV antigens in the Ortho 3.0 ELISA, and the like. The present invention was achieved by adding a reducing agent such as, for example, dithiothreitol (DTF) to the antigen diluent or buffer.

In a preferred embodiment of the invention, the HCV antigen diluent or buffer comprises a reducing agent. In another preferred embodiment of the invention, the HCV antigen diluent or buffer comprises sodium phosphate (pH 6.5), ethylenediaminetetraacetic acid (EDTA), DTT, gelatin, ammonium thiocyanate, sodium azide and SDS. However, these individual reagents can be replaced by similar reagents performing essentially the same function. For example, DTT can be replaced with additional reducing agents such as, for example, thioglycerol, mercaptoethenol, and the like. Sodium phosphate can be replaced by sodium borate and other buffers. Gelatin can be replaced with BSA and other blocking agents of non-specific binding. Sodium thiocyanate can be replaced with ammonium thiocyanate and other chaotropic agents. SDS can be replaced by a number of detergents such as, for example, Tween-20, and other detergents. Sodium azide can be replaced by other anti-bacterial agents. In addition, EDTA can be replaced by ethylene glycol-bis($\beta$-aminoethyl ether)-N,N,N',N'-tetraacetic acid (EGTA) and other chelating agents. One skilled in the art is familiar with reagents which can be substituted for those of the present invention.

In a preferred embodiment of the present invention, the HCV antigen diluent comprises from about 15 mM to about 100 mM sodium phosphate, pH 6.5. More preferably the diluent comprises from about 20 mM to about 75 mM sodium phosphate, pH 6.5. Most preferably, the diluent comprises 24 or 25 mM sodium phosphate, pH 6.5.

In another preferred embodiment of the present invention, the HCV antigen diluent comprises from about 1 mM to about 10 mM EDTA. More preferably the diluent comprises from about 3 mM to about 7 mM EDTA. Most preferably, the diluent comprises 5 mM EDTA.

In another preferred embodiment of the present invention, the HCV antigen diluent comprises from about 1 mM to about 200 mM DTT. More preferably the diluent comprises from about 5 mM to about 100 mM DTT. Most preferably, the diluent comprises 10 mM DTT.

In another preferred embodiment of the present invention, the HCV antigen diluent comprises from about 0.05% to about 1% gelatin. More preferably the diluent comprises from about 0.1% to about 0.5% gelatin. Most preferably, the diluent comprises 0.2% gelatin.

In another preferred embodiment of the present invention, the HCV antigen diluent comprises from about 10 mM to about 500 mM ammonium thiocyanate. More preferably the diluent comprises from about 50 mM to about 200 mM ammonium thiocyanate. Most preferably, the diluent comprises 100 mM ammonium thiocyanate.

In another preferred embodiment of the present invention, the HCV antigen diluent comprises from about 0.01% to about 0.3% sodium azide. More preferably the diluent comprises from about 0.05% to about 0.2% sodium azide. Most preferably, the diluent comprises 0.09% sodium azide.

In another preferred embodiment of the present invention, the HCV antigen diluent comprises from about 0.01% to about 0.5% SDS. More preferably the diluent comprises from about 0.05% to about 0.2% SDS. Most preferably, the diluent comprises 0.1% SDS.

In another preferred embodiment of the present invention, the HCV antigen diluent for the manual assay comprises 25 mM sodium phosphate, pH 6.5, 5 mM EDTA, 10 mM DTT, 0.2% gelatin, 100 mM ammonium thiocyanate, 0.09% sodium azide and 0.1% SDS.

For the automated assays, a preferred antigen buffer for c33c comprises 50 mM phosphate, 5 mM EDTA, 100 mM ammonium thiocyanate, 0.06% SDS, 0.25% fish gelatin and 10 mM DTF.

Table 1 shows a preferred HCV buffer.

TABLE 1

HCV Antigen Buffer For HCV Antigens

| Description | Concentration | Source | Product# | Lot# |
|---|---|---|---|---|
| Sodium Phosphate Monobasic | 25 mM | JT Baker | 3818-05 | A45101 |
| Sodium Azide | 0.09% | Fisher Biotech | BP922-500 | 953331 |
| EDTA | 5 mM | Fisher Chemical | S311-100 | 953493 |
| Sodium Thiocyanate | 100 mM | Sigma | S-7757 | 96HO543 |
| Tween-20 | 0.10% | Sigma | P-1379 | 56HO876 |
| Gelatin (fish) | 0.20% | Sigma | G-7765 | 45H1157 |
| DTT | 10 mM | Sigma | D-5545 | 26HO3801 |

The HCV antigen diluents or buffers of the present invention can be prepared by well known media preparation techniques. A preferred embodiment of preparing the HCV antigen diluents of the present invention is shown in Table 2.

TABLE 2

Process For Preparation Of Diluents

| Process Step | Amount |
|---|---|
| 1. Add 95% of batch quantity P-30 water | |
| 2. Add sodium phosphate, monobasic | 3.45 g/L |
| 3. Add sodium azide | 0.9 g/L |
| 4. Add EDTA | 1.86 g/L |
| 5. Add sodium thiocyanate | 8.1 g/L |
| 6. pH solution 6.5 ± 0.1 and stir | |
| 7. Add Tween-20 | 1 mL/L |
| 8. Add gelatin | 2 mL/L |
| 9. Add DTT | 1.54 g/L |
| 10. Stir solution until dissolved | |
| 11. Filter through 1.22 $\mu$m Millipak filter unit | |
| 12. Store at 4° C. in dark | |

The HCV antigen diluents or buffers of the present invention can be used in manual or automatic assays. The antigen diluents or buffers of the present invention can be used with numerous HCV antigens including, but not limited to, c33c, MEFA-6, c22p, c100p, NS5 and c200. These HCV antigens can be prepared by recombinant procedures routinely used in the art.

HCV c33c (NS3) and c100 (NS4) region sequences contain epitopes from the immunodominant core and were prepared as described in Chien, et al., *Proc. Natl. Acad. Sci. USA*, 1992, 89, 10011–10015. The c200 antigen is a fusion protein consisting of the c33c and c100 antigens. The c22 (119 amino acids) and NS5 (942 amino acids) antigens were expressed as internal antigens within the yeast *S. cerevisiae* as C-terminal fusions with human superoxide dismutase (SOD) using methods described previously for the generation of the c100—3 (363 amino acids) antigen. Kuo, et al., *Science*, 1989, 244, 362–364, incorporated herein by reference in its entirety; and Cousens, et al., *Gene*, 1987, 61, 265–275, incorporated herein by reference in its entirety.

The c33c antigen (363 amino acids) was expressed as an internal SOD fusion polypeptide in *E. coli* by methods described for the synthesis of 5-1-1 antigen. Choo, et al, *Science*, 1989, 244, 359–362, incorporated herein by reference in its entirety. The recombinant HCV antigens were purified as described in Chien, et al., *Proc. Natl. Acad. Sci. USA*, 1989, 89, 10011–10015. In the present invention, all HCV antigens were prepared as SOD fusion proteins. However, other suitable fusion proteins can be made depending upon the availability of appropriate antibodies that recognize the fusion partner.

MEFA-6 contains epitopes from the core, envelope, NS3, NS4 and NS5 regions of the hepatitis C polyprotein, including equivalent antigenic determinants from HCV strains 1, 2, and 3. The various DNA segments coding for the HCV epitopes were constructed by PCR amplification or by synthetic oligonucleotides. Table 3, below, describes the amino acid segments of each epitope, the linear arrangement of the various epitopes and the number of copies in the MEFA-6 cassette. MEFA-6 cassette was prepared as described in application PCT US97/08950 filed May 23, 1997, incorporated herein by reference in its entirety.

As shown in Table 3, the MEFA-6 antigen includes multiple copies of HCV epitopes from the core and NS5 region; different serotype epitopes from the NS4 5-1-1 region; a single copy of major linear epitopes from the c100 C-terminal regions, E1, and E2 regions, as well as the HCV NS3 (c33c) region. The general structural formula for MEFA-6 is hSOD-E1-E2-c33c-5-1-1(type 1)-5-1-1(type 3)-5-1-1 (type 2)-c100-NS5(2 copies)-core (2 copies). This antigen has a very high expression level in yeast, purifies to a high degree of homogeneity, and exhibits high sensitivity and high selectivity in the immunoassays described below. MEFA-6 was prepared as described in application Ser. No. 08/859,524 filed May 20, 1997, incorporated herein by reference in its entirety.

TABLE 3

MEFA-6 Antigen Epitopes And Their Location Within The HCV Genome

| MEFA aa# | 5' End Site | Epitope | HCV aa# | Strain |
|---|---|---|---|---|
| 1–154 | NcoI | hSOD | | |
| 159–176 | EcoRI | E1 | 303–320 | 1 |
| 179–217 | HindIII | E2 | 405–444 | 1 |
| 218–484 | DraIII | c33c | 1192–1457 | 1 |
| 487–533 | SphI | 5-1-1 | 1689–1735 | 1 |
| 536–582 | NruI | 5-1-1 | 1689–1735 | 3 |
| 585–631 | ClaI | 5-1-1 | 1689–1735 | 2 |
| 634–673 | AvaI | c100 | 1901–1940 | 1 |
| 676–711 | XbaI | NS5 | 2278–2313 | 1 |
| 714–749 | BglII | NS5 | 2278–2313 | 1 |
| 750–793 | NcoI | core | 10–53 | 1 |
| 796–839 | SacI | core | 10–53 | 1 |

The detectable marker may include, but is not limited to, a chromophore, an antibody, an antigen, an enzyme, an enzyme reactive compound whose cleavage product is detectable, rhodamine or rhodamine derivative, biotin, streptavidin, a fluorescent compound, a chemiluminscent compound, derivatives and/or combinations of these markers. In the present examples, the chemiluminescent compound dimethyl acridinium ester (DMAE, Ciba Corning Diagnostics Corp.) was used. Labeling with any marker is carried out under conditions for obtaining optimal detection and antigenicity of the MEFA-6 or other epitope. Where DMAE is the detectable marker in an assay, the resultant HCV r-Ag-DMAE conjugate is the tracer, with DMAE detectable by light emission when reacted with NaOH/$H_2O_2$.

A polypeptide, antibody or synthetic peptide antigen was labeled with DMAE by reaction of amino acid side chains (e.g. lysine ε side chain or cysteine thiol) with a reactive moiety covalendly linked to DMAE (see WO 95/27702, published Oct. 19, 1995, Ciba Corning Diagnostics Corp., herein incorporated by reference in its entirety). For example, the HCV antigens described herein were labeled by reaction with the amino groups of lysine side chains with NSP-DMAE-NHS (2', 6'-Dimethyl-4'-(N-succinimidyloxycarbonyl)phenyl-10-(3'-Sulfopropyl)-acridinium-9-carboxylate obtained from Ciba Corning. Thiols of amino acid side chains can be labeled using DMAE-ED-MCC or NSP-DMAE-PEG-BrAc (Ciba Corning). Labeling procedures were generally as described in WO 95/27702 with variations in conditions as necessary for each antigen to provide optimal detection and antigenicity.

EXAMPLES

Example 1

Manual Assay

A Magic Lite Analyzer System II (MLA II) is used for the manual assay. Parameters such as volume, concentration, time, and temperature are provided for guidance, but may be adjusted accordingly. Briefly, a 10 μl aliquot of test sample was added to corresponding tubes. The test sample is preferably a biological fluid (plasma or serum, for example) possibly containing anti-HCV antibodies, as well as proper controls. To each tube is added 100 μl of antigen diluent or buffer and incubated for 6 minutes at 37° C. To each tube is added 100 μl of solid phase buffer containing paramagnetic particles (PMP) conjugated to rat anti-human IgG antibodies (PMP/anti-human IgG) for a final concentration of approximately 60 μg/assay. However, other anti-human IgG antibodies are suitable. Preferably, the paramagnetic particles are less than approximately 10 μm in diameter. The PMP/anti-human IgG particles can be diluted in a diluent containing Tris buffer, pH 8.0, 150 mM NaCl, 2.75% BSA, 0.1% casein, 0.1% Tween-20, 0.1% yeast extract, 0.25% *E. coli* extract, 0.005% SOD, 0.09% $NaN_3$ and 1 mM EDTA. Subsequently, recombinant HCV antigens (HCV antigen/SOD fusion proteins) conjugated to DMAE (MEFA-6-DMAE, c33c-DMAE and c200DMAE, for example) are added in a 50 μl volume of ligand reagent (LR) diluent at a concentration of approximately 0.1 μg/assay to 1 μg/assay. Preferably, an amount of ligand reagent is added to each sample such that approximately 25×10$^6$ light unit equivalents (relative light units, RLU) are present per assay. This approximate amount of light unit equivalents is preferred for the addition of a single ligand, or for multiple ligands. LR diluent contains Tris buffer, pH 8.0, 150 mM NaCl, 1.0% BSA, 0.1% Tween-20, 0.09% $NaN_3$, and 1 mM EDTA. To ensure complete mixing, the tubes are shaken on a Vortex mixer 6 times at 5–10 seconds each time. The sample tubes are incubated at 37° C. for 18 minutes. The sample tubes are placed on a magnet for 3 minutes, for sufficient time to sediment the PMP particles. The samples are decanted using a magnet to retain the PMP particles. The PMP particles are washed twice with vortexing in 1 ml of PBS. The wash solution is PBS, 0.1% Tween-20, 0.09% $NaN_3$, and 1 mM EDTA. The steps of mixing, incubating, sedimenting and decanting may be repeated at least one time. To each tube 100 μl of water is added to resuspend the PMP particles. The tubes are then placed in an MLA-II instrument and light emission is measured for 2 seconds.

Example 2

Automated Assay

The manual anti-HCV assay described above was adapted for automated use using an ACS:Centaur apparatus. The following procedure is used. Briefly, the ACS:Centaur system automatically performs the following steps: 1) dispenses 10 μl of sample into a cuvette; 2) dispenses 100 μl of ancillary diluent buffer, 100 μl of Lite Reagent/Solid Phase, 50 μl of antigen reagent 2 (e.g., MEFA-6), 50 μl of antigen reagent 1 (e.g., c33c) and incubates the mixture for 18 minutes at 37° C.; 3) separates the solid phase from the mixture and aspirates the unbound reagent; 4) washes the cuvette with wash reagent 1; 5) dispenses 300 μl each of acid reagent and base reagent to initiate the chemiluminescent reaction; and 6) reports results according to the selected option, as described in the system operating instructions or in the online help system. The solid phase/Lite reagent diluent buffer comprises 50 mM Tris, 0.5 M KCl, 1 mM EDTA, 3.75% BSA, 0.003% Yeast, 0.05g/L $E.$ $coli,$ 0.5% Tween-20, 2 mg/L Amphotericin B, 24 mg/L Gentamicin Sulfate, 30 μg/test Solid Phase and $45 \times 10_6$ test Lite Reagent (anti-SOD*DMAE antibodies). The ancillary diluent buffer comprises 50 mM Tris, 0.5M KCl, 1 mM EDTA, 3.75% BSA, 0.003% Yeast, 0.05 g/L $E.$ $coli,$ 0.5% Tween-20, 2 mg/L Amphotericin B, 24 mg/L Gentamicin Sulfate, 0.05 g/L Ascites IgGI and 0.1 g/L Ascites IgG2A (blocking antibodies). The wash reagent comprises PBS/Tween-20. The acid reagent comprises 0.5% $H_2O_2$/0.1 N $HNO_3$. The base reagent comprises <0.25N NaOH with surfactant.

Example 3

Manual Assay with c33c

A manual assay using c33c HCV antigen was performed with 100 ng of c33c per assay using the methodology described above in Example 1. The antigen diluent comprised 25 mM sodium phosphate, pH 6.5, 100 mM sodium thiocyanate, 5 mM EDTA, 0.1% Tween-20, 0.2% fish gelatin, 0.09% sodium azide and 10 mM DTT. The assay was performed with $3 \times 10_6$ RLU/10 μl, 30 μg/assay PMP. The assay was performed at varying times and under varying temperatures. For example, the assay was performed at Day 0 at 40° C., at Day 3 at 4° C., at Day 1 at 37° C., at Day 2 at 37° C., at Day 3 at 37° C. and at Day 6 at 37° C.

A 10 μl sample (such as a biological fluid containing human anti-HCV antibodies) was added to each sample tube. Samples included: random negative controls (r1, r2 and r3), a positive control (Virotrol), seroconversion panels (PHV905-5, PHV907-4 and PHV904-6), HCV patient samples (FF25931) and seroconversion samples (6214-09 and 6212-04). The results are shown in Table 4. Sensitivity was reported as the optical density of the assay sample divided by the assay detection cut off in optical density units (s/co). All known negative samples exhibited relative light units (RLU) below the cutoff value, while known positive samples exhibited RLUs well above the cutoff value.

For comparative purposes, the detection of HCV antibodies from some of the samples (see Table 4) was also performed by Ortho 3.0 and a commercial strip immunoblot assay (RIBA® 3.0 Chiron Corporation), which assay is used clinically as a confirmatory test for HCV antibody detection. According to the RIBA® method, recombinant HCV antigens are separated by gel electrophoresis and contacted with patient serum. Reactivity with the separated antigens is performed by immunoblot assay using secondary labeled antibodies. Assay results are scored on a plus/minus scale. Eheling, et al., *Lancet,* 1991, 337, 912–913, incorporated herein by reference in its entirety. The Ortho 3.0 assay was performed according to the manufacturer's instructions. c33c, c22p, c100p, and NS-5 were used as the HCV antigens for these tests.

Briefly, the RIBA® 3.0 assay was performed as follows. Approximately 30 minutes before beginning the assay, the kit was removed from refrigeration (2 to 8° C.) and the components of the kit allowed to come to room temperature (15 to 30° C.). The required number of strips were removed from the sealed foil pouches and placed in the assay tube rack in their respective tubes. One ml of Specimen Diluent was added to each tube so that the entire strip was covered with liquid. Twenty μl of the appropriate specimen or control was added to the corresponding tube. The tubes were capped and inverted to mix. The rack with the tubes was placed on a rocker and fastened with rubber bands or tape; the rack was rocked (at 16–20 cycles/minute) for 4 to 4½ hours at room temperature (15 to 30° C.). The tubes were uncapped and the liquid was completely aspirated into a waste container. One ml of Specimen Diluent was added to each tube. The tubes were capped and placed on the rack on the rocker and rocked for 30 to 35 minutes at room temperature. The liquid was then aspirated. One ml of Working Wash Buffer was added to each tube, then the liquid and strips poured into wash vessels containing 30 ml of Working Wash Buffer (maximum 20 strips per wash vessel). The wash vessels were completely filled with Working Wash Buffer (60 mL total volume), then the wash was decanted. To retain the strips, the wash vessel was gently rolled while decanting. Sixty ml of Working Wash Buffer was added, swirled, then the wash was decanted the while retaining the strips. One ml of Conjugate per strip was added to each wash vessel (minimum 10 ml per wash vessel). The wash vessels were rotated on a rotary shaker at 110±5 rpm for 9 to 11 minutes at room temperature (15 to 30° C.). Working Substrate was prepared up to 1 hour prior to use. Upon completion of Conjugate incubation, the Conjugate was decanted and the strips were washed by adding 60 ml of Working Wash Buffer and swirling. The wash was decanted and this step was repeated two more times. The fmal wash was decanted. One ml of Working Substrate was added per strip to each wash vessel (minimum 10 ml per wash vessel). The wash vessels were rotated on a rotary shaker at 110±5 rpm for 15 to 20 minutes at room temperature (15 to 30° C.). The Working Substrate was decanted and the strips were washed by adding 60 ml of distilled or deionized water and swirling. The wash was decanted and this step was repeated one more time. To retain strips, the wash vessel was gently rolled while decanting. Using forceps, the strips were transferred to absorbent paper and excess water was blotted. The strips were air-dried in the dark for at least 30 minutes at room temperature. The strips were interpreted within 3 hours. Anti-HCV reactivity in a specimen was determined by comparing the intensity of each antigen band to the intensity of the human IgG (Level I and Level II) internal control bands on each strip. The identity of the antibodies was defined by the specified location of the antigen band. The intensity of the antigen/peptide bands was scored in relation to the intensities of the internal IgG controls as follows: absent (-), less than intensity of the Level I IgG control band (-/+), equal to intensity of the Level I IgG control band (1+), greater than intensity of the Level I IgG control band and less than intensity of the Level II IgG control band (2+), equal to intensity of the Level II IgG control band (3+), and greater than intensity of the Level II IgG control band (4+).

Example 4

Manual Assay with c200

A manual assay using c200 HCV antigen was performed as described in Example 1 with various amounts of reducing agent. The stabilizing buffer was the same as in Example 3, except for the amount of reducing agent. The assay was performed with 3×10⁶ RLU/10 μl, 30 μg/assay PMP. The assay was performed at varying times and under varying amounts of reducing agent. For example, the assay was performed after 1 day at 37° C. with 20 mM DTT (Vial I), after 1 day at 37° C. without DTT (Vial II), and after 1 day at 37° C. where 20 mM DTT was added prior to testing (Vial III. Vials II and III were also tested after 3 days.

A 10 μl sample (such as a biological fluid containing human anti-HCV antibodies) was added to each sample tube. Samples included: random negative controls (r1, r2, r3, r4 and r5), seroconversion panels (PHV904-6 and PHV906-1) and HCV patient samples (FF25931) at various dilutions. The results are shown in Table 5. s/n is the sensitivity divided by the value ave. neg.

Example 5

Manual Assay with MEFA-6 and c33c

A manual assay using MEFA-6 and c33c HCV antigen was performed with 100 ng of MEFA-6 and 85 ng of c33c per assay using the methodology described above in Example 1. The stabilizing buffer for MEFA-6 comprised 50 mM sodium borate, pH 9.5, 5 mM EDTA, 0.05% Tween-20, 0.5% BSA, and 1% thioglycerol. At this pH 9.5 MEFA-6 is stable so no reducing agent is necessary. The buffer for c33c comprised 25 mM sodium phosphate, pH 6.5, 5 mM EDTA, 0.1% Tween-20, 0.2% fish gelatin, 100 mM sodium thiocyanate, and 10 mM DTT. The assay was performed with 4.5×10⁶ RLU/10 μl of anti-SOD*DMAE, 30 μg/assay PMP. The assay was performed at varying times and under varying temperatures. For example, the assay was performed at Day 7 at 4° C. and at Day 7 at 37° C.

A 10 μl sample (such as a biological fluid containing human anti-HCV antibodies) was added to each sample tube. Samples included, random negative controls (r1, r2, r3 and r4), a positive control (Virotrol), seroconversion panels (PHV905-5, PHV909-1, PHV909-2 and PHV909-3), seroconversion samples (6212-02 and 6214-09) and seroconversion control panels (SC-0030A, SC-0030B, SC-0030C, SC-0030D, SC-0040A, SC-0040B, SC-0040C, SC-0040D and SC-0040E). The results are shown in Table 6. Sensitivity was reported as the optical density of the assay sample divided by the assay detection cut off in optical density units (s/co). All known negative samples exhibited relative light units (RLU) below the cutoff value, while known positive samples exhibited RLUs well above the cutoff value.

For comparative purposes, the detection of HCV antibodies from some of the samples (see Table 6) was also performed by Ortho 3.0 and RIBA® 3.0 as described in Example 3.

Example 6

Manual Assay with MEFA-6

A manual assay using MEFA-6 HCV antigen was performed with 100 ng of MEFA-6 per assay using the methodology described above in Example 1. The buffer for MEFA-6 comprised 50 mM sodium borate, pH 9.5, 5 mM EDTA, 0.05% Tween-20, 0.5% BSA, and 1% thioglycerol. The assay was performed with 4.5×10⁶ RLU/10 μl of anti-SOD*DMAE, 30 μg/assay PMP. The assay was performed at Day 7 at 4° C.

A 10 μl sample (such as a biological fluid containing human anti-HCV antibodies) was added to each sample tube. Samples included, random negative controls (r1, r2 and r3), positive control (Virotrol) and seroconversion control panels (SC-0030A, SC-0030B, SC-0030C and SC0030D). The results are shown in Table 7. Sensitivity was reported as the optical density of the assay sample divided by the assay detection cut off in optical density units (s/co). All known negative samples exhibited relative light units (RLU) below the cutoff value, while known positive samples exhibited RLUs well above the cutoff value.

For comparative purposes, the detection of HCV antibodies from some of the samples (see Table 7) was also performed by Ortho 3.0 and RIBA® 3.0 as described above. The foregoing examples are meant to illustrate the invention and are not to be construed to limit the invention in any way. Those skilled in the art will recognize modifications that are within the spirit and scope of the invention. All references cited herein are hereby incorporated by reference in their entirety.

TABLE 4 c33c Assay

| Sample | Day 0 4° C. | Day 3 4° C. | Day 1 37° C. | Day 2 37° C. | Day 3 37° C. | Day 6 37° C. |
|---|---|---|---|---|---|---|
| r1 | 1925 | 1247 | 1001 | 1509 | 1971 | 2202 |
| r2 | 1740 | 1679 | 1632 | 1448 | 1401 | 1863 |
| r3 | 1602 | 1432 | 1463 | 1401 | 1725 | 1940 |
| Virotrol | 61708 | 64156 | 65604 | 60060 | 56595 | 59044 |
| 6214-09 | 14322 | 16555 | 10888 | 16555 | 14784 | 15246 |
| 6212-04 | 40856 | 43351 | 41842 | 40225 | 36421 | 39008 |
| PHV905-5 | 10734 | 15030 | 14969 | 13721 | 15785 | 13999 |
| PHV907-4 | 2341 | 1756 | 1940 | 2017 | 2110 | 2002 |
| PHV904-6 | 53299 | 49496 | 54208 | 54285 | 47155 | 45676 |
| FF25931 1.8 | 567120 | 608993 | 530006 | 572603 | 568974 | 581504 |
| ave. neg. | 1756 | 1453 | 1365 | 1453 | 1699 | 2002 |
| cutoff | 5267 | 4358 | 4096 | 4358 | 5097 | 6005 |

| | s/co | s/co | s/co | s/co | s/co | s/co | RIBA 3.0 | | | | ORTHO 3.0 |
|---|---|---|---|---|---|---|---|---|---|---|---|
| | | | | | | | c33c | c22p | c100p | NS-5 | s/co |
| Virotrol | 11.72 | 14.72 | 16.02 | 13.78 | 11.10 | 9.83 | | | | | |
| 6214-09 | 2.72 | 3.80 | 2.66 | 3.80 | 2.90 | 2.54 | 2+ | − | +/− | − | 0.9 |
| 6212-04 | 7.76 | 9.95 | 10.22 | 9.23 | 7.15 | 6.50 | 1+ | − | − | − | 1.4 |

TABLE 4-continued c33c Assay

| | | | | | | | | | | | |
|---|---|---|---|---|---|---|---|---|---|---|---|
| PHV905-5 | 2.04 | 3.45 | 3.65 | 3.15 | 3.1 | 2.33 | 1+ | – | – | – | 0.9 |
| PHV907-4 | 0.44 | 0.40 | 0.47 | 0.46 | 0.41 | 0.33 | – | 1+ | – | – | 0.1 |
| PHV904-6 | 10.12 | 11.36 | 13.23 | 12.46 | 9.25 | 7.61 | 2+ | – | – | – | >5.0 |

TABLE 5 c200 Assay

| Sample | Vial I 37° C. Day 1 control c200 20 mM DTT | Vial II 37° C. Day 1 test c200 w/o DTT | Vial III 37° C. Day 1 test c200 added 20 mM DTT | Vial III 37° C. Day 1 test c200 added 40 mM DTT | Vial III 37° C. Day 3 test c200 added 40 mM DTT | Vial III 37° C. Day 3 test c200 w/o DTT |
|---|---|---|---|---|---|---|
| random r1 | 1463 | 1448 | 1078 | 1109 | 1217 | 801 |
| random r2 | 1217 | 1324 | 1247 | 1879 | 1309 | 1016 |
| random r3 | 1155 | 1247 | 1340 | 1217 | 1063 | 1124 |
| random r4 | 1170 | 1217 | 2402 | 1340 | 1386 | 1140 |
| random r5 | 1155 | 1232 | 1217 | 1494 | | |
| serocon. PHV904-6 | 29106 | 10102 | 8763 | 13182 | 14060 | 2141 |
| serocon. PHV906-1 | 27828 | 15231 | 16016 | 21468 | 30523 | 25656 |
| FF25931 1:4 | 643551 | 574944 | 435543 | 318025 | 322307 | 277616 |
| FF25931 1:256 | 26657 | 19774 | 16339 | 16524 | 22484 | 21699 |
| FF25931 1:1024 | 9948 | 7854 | 8516 | 8408 | 12859 | 17048 |
| ave. neg. | 1232 | 1294 | 1457 | 1408 | 1244 | 1020 |
| | s/n | s/n | s/n | s/n | s/n | s/n |
| serocon. PHV904-6 | 23.6 | 7.8 | 6.0 | 9.4 | 11.3 | 2.1 |
| serocon. PHV906-1 | 22.6 | 11.8 | 11.0 | 15.2 | 24.5 | 25.1 |
| FF25931 1:4 | 522.4 | 444.5 | 299.0 | 225.9 | 259.1 | 272.1 |
| FR25931 1:256 | 21.6 | 15.3 | 11.2 | 11.7 | 18.1 | 21.3 |
| F2F5931 1:1024 | 8.1 | 6.1 | 5.8 | 6.0 | 10.3 | 16.7 |

TABLE 6

MEFA-6 + c33c Assay

| Sample | 4° C. Day 7 s | 4° C. Day 7 s/co | 37° C. Day 7 s | 37° C. Day 7 s/co | Ortho 3.0 s/co | RIBA 3.0 c100p | 3.0 c33c | c22p | NS-5 | Genotype |
|---|---|---|---|---|---|---|---|---|---|---|
| NABI SC-0030A | 6607 | 0.39 | 5960 | 0.43 | 0.005 | – | – | – | – | 1a |
| NABI SC-0030B | 14522 | 0.86 | 8778 | 0.64 | 0.015 | 3+ | +/– | +/– | – | |
| NABI SC-0030C | 86748 | 5.12 | 46785 | 3.40 | 1.837 | 4+ | 1+ | 2+ | – | |
| NABI SC-0030D | 472749 | 27.92 | 489304 | 35.54 | 4.900 | 4+ | 4+ | 4+ | 3+ | |
| NABI SC-0040A | 9379 | 0.55 | 7454 | 0.54 | 0.003 | – | – | – | – | 2b |
| NABI SC-0040B | 12720 | 0.75 | 7546 | 0.55 | 0.056 | – | – | – | – | |
| NABI SC-0040C | 65927 | 3.89 | 29799 | 2.16 | 1.215 | +/– | 2+ | – | – | |
| NABI SC-0040D | 106845 | 6.31 | 43613 | 3.17 | 1.534 | +/– | 2+ | – | – | |
| NABI SC-0040E | 175067 | 10.34 | 78124 | 5.67 | 3.247 | 1+ | 3+ | 1+ | – | |
| random r1 | 5236 | | 4697 | | | | | | | |
| random r2 | 5652 | | 4112 | | | | | | | |
| random r3 | 5991 | | 5375 | | | | | | | |
| random r4 | 5698 | | 4173 | | Ortho 3.0 s/co | RIBA 3.0 c100p | 3.0 c33c | c22p | NS-5 | |
| control Virotrol I | 117548 | 6.94 | 74721 | 5.43 | | | | | | |
| BCP 6212-04 | 68807 | 4.06 | 31616 | 2.30 | 1.4 | – | 1+ | – | – | |
| BCP 6214-09 | 81543 | 4.82 | 24270 | 1.76 | 0.9 | +/– | 2+ | – | – | |
| BBI PHV905-5 | 25040 | 1.48 | 16755 | 1.22 | 0.9 | – | 1+ | – | – | |
| BBI PHV909-1 | 6699 | 0.40 | 5313 | 0.39 | 0.0 | – | – | – | – | |
| BBI PHV909-2 | 30661 | 1.81 | 15646 | 1.14 | 1.3 | – | – | 1+ | +/– | |
| BBI PHV909-3 | 32432 | 1.92 | 16570 | 1.20 | 1.4 | – | – | 2+ | +/– | |
| ave. neg. | 5644 | | 4589 | | | | | | | |
| cutoff | 16933 | | 13768 | | | | | | | |

TABLE 7

MEFA-6 Assay

| Sample | 4° C. s | Day 7 s/co | Ortho 3.0 s/co | RIBA 3.0 c100p | c33c | c22p | NS-5 | Genotype |
|---|---|---|---|---|---|---|---|---|
| random r1 | 8624 | | | | | | | |
| random r2 | 8609 | | | | | | | |
| random r3 | 7192 | | | | | | | |
| control Virotrol I | 129406 | 5.00 | | | | | | |
| NABI SC-0030A | 8516 | 0.33 | 0.005 | – | – | – | – | 1a |
| NABI SC-0030B | 26827 | 1.04 | 0.015 | 3+ | +/– | +/– | – | |
| NABI SC-0030C | 179980 | 6.96 | 1.837 | 4+ | 1+ | 2+ | – | |
| NABI SC-0030D | 508831 | 19.67 | 4.900 | 4+ | 4+ | 4+ | 3+ | |
| ave. neg. | 8624 | | | | | | | |
| cutoff | 25872 | | | | | | | |

We claim:

1. An antigen diluent or buffer comprising a reducing agent, a buffering agent, a chelating agent, a blocking agent of non-specific binding, a chaotropic agent, an antibacterial agent, and a detergent.

2. The antigen diluent or buffer of claim 1 wherein the reducing agent is selected from the group consisting of dithiothreitol (DTT), thioglycerol, and mercaptoethanol.

3. The antigen diluent or buffer of claim 1 wherein the reducing agent is DTT.

4. The antigen diluent or buffer of claim 3 wherein the concentration of DTT is from about 1 mM to about 200 mM.

5. The antigen diluent or buffer of claim 3 wherein the concentration of DTT is from about 5 mM to about 100 mM.

6. The antigen diluent or buffer of claim 3 wherein the concentration of DTT is about 10 mM.

7. The antigen diluent or buffer of claim 1 wherein the buffering agent is sodium phosphate or sodium borate.

8. The antigen diluent or buffer of claim 7 wherein the buffering agent is sodium phosphate.

9. The antigen diluent or buffer of claim 8 wherein the concentration of sodium phosphate, pH 6.5, is from about 15 mM to about 100 mM.

10. The antigen diluent or buffer of claim 1 wherein the chelating agent is ethylenediaminetetraacetic acid (EDTA).

11. The antigen diluent or buffer of claim 10 wherein the concentration of EDTA is from about 1 mM to about 10 mM.

12. The antigen diluent or buffer of claim 1 wherein the detergent is sodium dodecyl sulfate (SDS) or polyoxyethylenesorbitan monolaurate.

13. The antigen diluent or buffer of claim 12 wherein the detergent is SDS.

14. The antigen diluent or buffer of claim 13 wherein the concentration of SDS is from about 0.01% to about 0.5%.

15. The antigen diluent or buffer of claim 1 wherein the anti-bacterial agent is sodium azide.

16. The antigen diluent or buffer of claim 15 wherein the concentration of sodium azide is from about 0.01% to about 0.3%.

17. The antigen diluent or buffer of claim 1 wherein the blocking agent of non-specific binding is gelatin or bovine serum albumin.

18. The antigen diluent or buffer of claim 17 wherein the blocking agent of non-specific binding is gelatin.

19. The antigen diluent or buffer of claim 18 wherein the concentration of gelatin is from 0.05% to about 1.0%.

20. The antigen diluent or buffer of claim 1 wherein the chaotropic agent is sodium thiocyanate or ammonium thiocyanate.

21. The antigen diluent or buffer of claim 20 comprising 25 mM sodium phosphate, pH 6.5, 5 mM EDTA, 10 mM DTT, 0.2% gelatin, 100 mM ammonium thiocyanate, 0.09% sodium azide and 0.1% SDS.

22. The antigen diluent or buffer of claim 20 comprising 50 mM sodium phosphate, 5 mM EDTA, 100 mM ammonium thiocyanate, 0.06% SDS, 0.25% fish gelatin and 10 mM DTT.

23. The antigen diluent or buffer of claim 1 wherein the buffering agent is sodium phosphate, the chelating agent is EDTA, the blocking agent of non-specific binding is gelatin, the chaotropic agent is sodium thiocyanate, the antibacterial agent is sodium azide, and the detergent is SDS.

24. An immunoassay kit for detection of hepatitis C virus (HCV) antibodies comprising an antigen diluent or buffer of claim 1.

25. The immunoassay kit of claim 24 wherein the reducing agent is selected from the group consisting of DTT, thioglycerol and mercaptoethanol.

26. The immunoassay kit of claim 25 wherein the reducing agent is DTT.

27. A composition comprising at least one antigen and an antigen diluent or buffer of claim 1.

28. A composition comprising at least one HCV antigen and an antigen diluent or buffer of claim 1.

29. A method of stabilizing an antigen comprising contacting the antigen with a diluent or buffer of claim 1.

* * * * *